United States Patent
Duglio et al.

(10) Patent No.: US 10,408,851 B2
(45) Date of Patent: Sep. 10, 2019

(54) DEVICE AND METHOD OF IDENTIFICATION AND MONITORING OF A REAGENT KIT OF AN ANALYTICAL SYSTEM

(71) Applicant: TECHNOGENETICS HOLDINGS S.R.L., Milan (IT)

(72) Inventors: Francesco Duglio, Vizzolo Predabissi (IT); Adolfo Cavallari, Caserta (IT); Luca Melillo, Lioni (IT)

(73) Assignee: Altergon Italia S.R.L., Pietradefusi (AV) (IT)

( * ) Notice: Subject to any disclaimer, the term of this patent is extended or adjusted under 35 U.S.C. 154(b) by 326 days.

(21) Appl. No.: 14/895,621

(22) PCT Filed: Jun. 11, 2014

(86) PCT No.: PCT/IB2014/062126
§ 371 (c)(1),
(2) Date: Dec. 3, 2015

(87) PCT Pub. No.: WO2014/199310
PCT Pub. Date: Dec. 18, 2014

(65) Prior Publication Data
US 2016/0124007 A1    May 5, 2016

(30) Foreign Application Priority Data
Jun. 11, 2013   (IT) ............... MI2013A0958

(51) Int. Cl.
*G01N 35/00* (2006.01)
*G01P 15/08* (2006.01)
(Continued)

(52) U.S. Cl.
CPC ....... *G01N 35/00732* (2013.01); *G01D 9/005* (2013.01); *G01D 21/00* (2013.01);
(Continued)

(58) Field of Classification Search
CPC ............... G01N 35/00732; G01D 9/005
(Continued)

(56) References Cited

U.S. PATENT DOCUMENTS

| | | |
|---|---|---|
| 2004/0167837 A1 | 8/2004 | Reel et al. |
| 2005/0087235 A1 | 4/2005 | Skorpik et al. |

(Continued)

FOREIGN PATENT DOCUMENTS

WO    2012/058770 A1    5/2012

OTHER PUBLICATIONS

International Search Report dated Aug. 26, 2014, issued in PCT Application No. PCT/IB2014/062126, filed Jun. 11, 2014.

*Primary Examiner* — Ricky Ngon
(74) *Attorney, Agent, or Firm* — Workman Nydegger

(57) ABSTRACT

A device is adapted to identify and monitor a reagent kit adapted for insertion into an analytical system, the device is positioned in the reagent kit and includes: apparatus for measuring the temperature of the reagent kit; apparatus for measuring the light level to which the reagent kit is subjected; apparatus for measuring the electric conductivity level of the reagent kit; means for measuring the triaxial acceleration to which the reagent kit is subjected; a multi-parameter data-logger for logging the data obtained from the temperature, light, conductivity and acceleration measuring apparatus; apparatus for storage and short-range transmission of data identifying the reagent kit and the data obtained from the temperature, light, conductivity and acceleration measuring apparatus, in order to detect operational or non-operational conditions of the kit.

9 Claims, 2 Drawing Sheets

(51) Int. Cl.
*G01D 9/00* (2006.01)
*G01D 21/00* (2006.01)
*G01J 1/42* (2006.01)
*G01N 25/00* (2006.01)
*G01N 27/04* (2006.01)
*G01P 15/00* (2006.01)

(52) U.S. Cl.
CPC ............... *G01J 1/42* (2013.01); *G01N 25/00* (2013.01); *G01N 27/04* (2013.01); *G01P 15/00* (2013.01); *G01P 15/0891* (2013.01)

(58) Field of Classification Search
USPC ........................................................ 702/179
See application file for complete search history.

(56) References Cited

U.S. PATENT DOCUMENTS

| | | | |
|---|---|---|---|
| 2008/0159913 A1* | 7/2008 | Jung | ................. A61B 5/14532 422/400 |
| 2010/0180701 A1 | 7/2010 | Daniel et al. | |
| 2012/0015444 A1* | 1/2012 | Mazumdar | ............. B01L 3/502 436/169 |
| 2014/0199758 A1* | 7/2014 | Aviv | ................... G01N 33/728 435/288.7 |

* cited by examiner

DEVICE AND METHOD OF IDENTIFICATION AND MONITORING OF A REAGENT KIT OF AN ANALYTICAL SYSTEM

FIELD OF THE INVENTION

The present invention relates to a device and a method for identifying and monitoring a reagent kit of an analytical system.

BACKGROUND ART

The reagent kit is a key element of a conventional and/or immunochemistry analytical system.

An analytical system is a machine for automatic execution of laboratory tests, requiring minimal intervention by the operator. Tests require preparation and dosage of biological samples and reagents, and identification thereof.

During the automatic test, fluids are mixed in the desired proportions, incubated, and analyzed as a function of the specific reaction involved. At the end of the measurements, the data are processed and presented by suitable software.

Reagents are the most important part of the system, because they allow to identify a wide range of composite analytes within biological fluids.

A reagent kit includes separate containers for a number of components, typically including diluents, reagents and calibrators.

A reagent kit is interchangeable, so that it can be replaced when exhausted or when the desired test type is changed. The kit is subject to autonomous production, transportation and storage (with respect to the analytical system). Each one of these stages has criticities due to potential content damage or alteration, depending on the desired quality and reliability of the measurements.

Therefore, for properly using the reagent kit, it is necessary to precisely identify it and be sure that it has been correctly stored and handled, so that it has not been subject to stresses that might have impaired its analytical performance.

For correctly managing the analytical system (reagent kit and instrument), it is also useful to have information about environmental events and about the presumed chemical-physical state of the reagents, so as to be able to find causes and take adequate corrective actions.

To ensure optimal performance, the man skilled in the art of developing analytical systems and reagent kits has to face a number of problems. Such problems require specific solutions for which it is de facto impossible to draw on other fields for usable technical knowledge.

Various types of sensors, as well as applications thereof in different technical fields, have been known for a long time. A passive or active RF-ID device is also per se known. The general notoriety of the above does not imply that they can obviously be used in the specific sector of developing an analytical system and a reagent kit.

For example, US2010/0180701-A1 describes a sensor device in the form of adhesive tape, to which different remote units are connected, each comprising one or more sensors, applicable in an adhesive manner to an object with a curved surface, such as a helmet, and electrically connected to a controller mounted on the adhesive tape itself. It is apparent that the system is not suitable for application within the technical scope of the present invention.

SUMMARY OF THE INVENTION

It is therefore the object of the present invention to propose a device and a method for identifying and monitoring a reagent kit for analytical systems which can overcome all of the above drawbacks.

The invention allows to identify the reagent kit and to collect data about the transportation, preservation and manipulation thereof from production to use in the analytical apparatus, for the purpose of:
- integrating information useful for the execution of the analytical routine;
- provide real-time information about the conditions of the kit during the test, in order to ensure measurement accuracy;
- making decisions, such as replacing the kit or modifying its expiry date;
- using collected information to optimize newly developed reagent kits and the analytical machines themselves.

To this end, the invention proposes a device based on the use of a semi-passive RFID (i.e., equipped with a battery for supplying power to microchips and sensors, but with a transmitter behaving like a passive tag) to be applied to the specific reagent kit, which, in addition to the identification function, also carries out a function as a multiparameter data-logger, thanks to the integration of temperature, light exposure, conductivity and triaxial acceleration sensors.

Furthermore, the device includes an acquisition and processing unit that can handle and store the signals coming from the sensors with minimal consumption, wherein the acquisition can be activated periodically or when certain thresholds of all quantities being monitored are exceeded.

The acquired data are stored and then transferred to the management software of the analytical system into which said reagent kit is inserted. This allows to evaluate the preservation condition thereof and to highlight any criticities.

Any critical conditions detected may also generate alarms or alert states, which can be used for finding the causes of reagent degradation and taking corrective actions.

It is one object of the present invention to provide a device adapted to identify and monitor a reagent kit adapted for insertion into an analytical system, characterized in that the device is positioned in said reagent kit and comprises:
- means for measuring the temperature of the reagent kit;
- means for measuring the light level to which the reagent kit is subjected;
- means for measuring the electric conductivity level of the reagent kit;
- means for measuring the triaxial acceleration to which the reagent kit is subjected;
- a multiparameter data-logger for logging the data obtained from said temperature, light, conductivity and acceleration measuring means;
- means for storage and short-range transmission of data identifying the reagent kit and said data obtained from said temperature, light, conductivity and acceleration measuring means, in order to detect operational or non-operational conditions of said kit.

It is a particular object of the present invention to provide a device and a method for identifying and monitoring a reagent kit of an analytical system as set out in the claims, which are an integral part of the present description.

BRIEF DESCRIPTION OF THE DRAWINGS

Further objects and advantages of the present invention will become apparent from the following detailed description of a preferred embodiment (and variants) thereof and from the annexed drawings, which are only supplied by way of non-limiting example, wherein.

In the drawings, the same reference numerals and letters identify the same items or components.

DETAILED DESCRIPTION OF SOME EMBODIMENTS OF THE INVENTION

Figure 1:
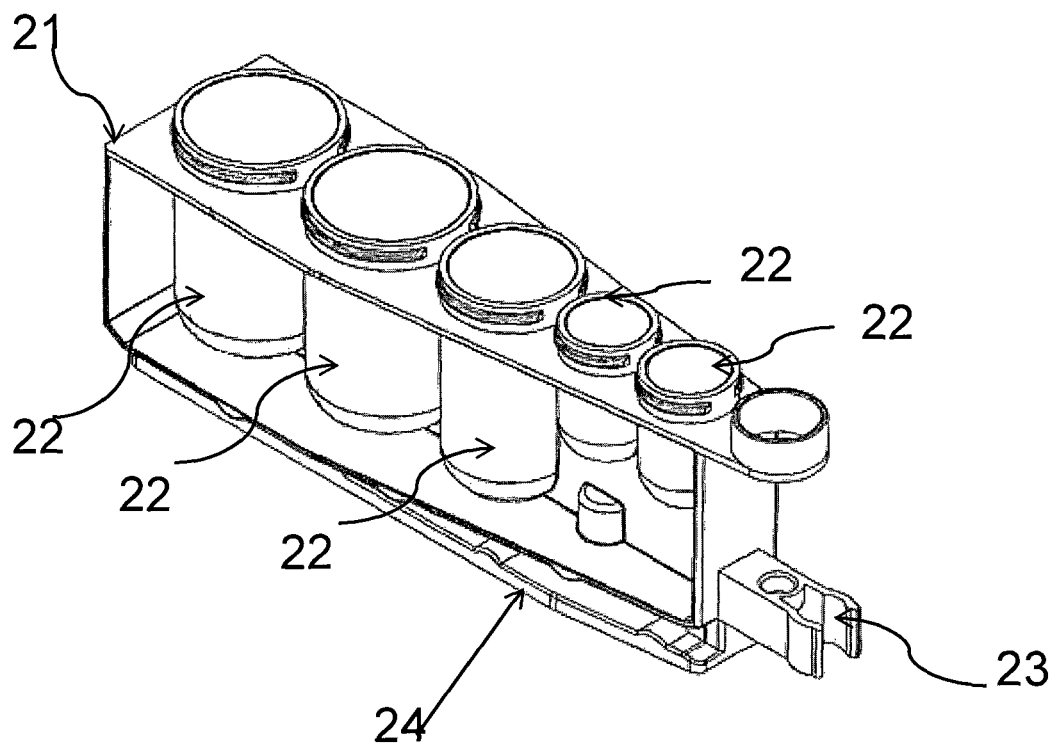
FIG. 1 shows one example of embodiment of a reagent kit, indicating the point whereto the RFID system is applied.

FIG. 1 shows an example of a typical reagent kit. It comprises an external casing 21, which may be either open on some sides or closed, with a shape suitable for stable insertion into a dedicated seat in the analytical system (not shown in the drawing). Within the casing there are a number of containers 22 for reagents and/or diluents and/or calibrators. In addition, a solid-phase mixing container is normally included (which is inserted in the position 23 shown in FIG. 1), which, as is known, contains a liquid and magnetic microparticles that are constantly mixed when the kit is aboard the machine, in order to prevent the particles from sedimenting on the bottom.

The identification and monitoring device is positioned in the reagent kit into a suitable seat 24 into the bottom part of the kit, so as to allow for short-range reading of the kit data into the analytical system by a reader positioned on the reagent plate of the analytical system.

The identification and monitoring device according to the invention comprises elements adapted to carry out the following functions:
  kit identification
  setting thresholds and modes of operation of the system
  multiparameter data-logging, with temperature, light, conductivity and triaxial acceleration sensors integrated into the device
  transmission of stored and current data, sensor signals and alarm conditions.

Figure 2:
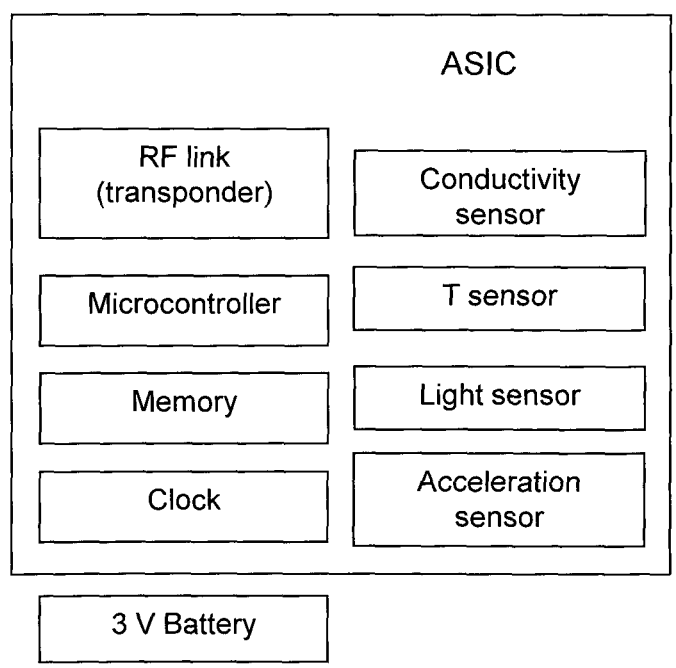
FIG. 2 shows a block diagram of the device according to the present invention.

With reference to FIG. 2, the identification and monitoring device is constituted by a number of components comprising ASIC integrated chips, with sensor elements, supply and conditioning system, battery, memory with radio-frequency interface.

More in particular, the system comprises:
  a microcontroller
  a real-time clock system (RTC)
  a memory unit
  an RFID with transponder
  a temperature sensor T
  a light sensor
  a conductivity sensor
  a MEMS triaxial acceleration sensor
  a battery The transmission/reception function via transponder is effected by means of a short-range connection (e.g., up to 10 centimeters) when transferring the reagent kit aboard the analytical system and during use, so as to allow for specific reading of the kit with respect to other nearby kits.

The system's operating band may be comprised in the range of 125 kHz to 433 MHz, including the 13.56 MHz NFC band used for experimentation.

The power supply battery of the device can be a low-capacity (48 mAh) button-type lithium battery, due to the low current absorption of the device.

It is assumed that the temperature of the reagent kit must be maintained within a certain range of values, e.g., 2-8° C. Therefore, the temperature sensor measures and records temperature values at regular intervals starting from a certain activation instant (e.g., production), until the reagent kit is inserted into the analytical system, or upon request when connecting it to the reader included in the system's base station.

The temperature sensor, just like the light, conductivity and acceleration sensors, can be made by using commercial components commonly used for consumer products and industrial controllers.

The components are integrated as standard cells into the ASIC, and take advantage of a serial interface with an integrated converter calibrated for the physical quantities of interest. In the case of temperature, the resolution is better than 0.1° C., with programmable threshold, event wake-up, and minimal consumption (10 to 100 μW).

As concerns light exposition, it is assumed that the reagent kit must nominally be preserved in the dark. Therefore, the light sensor is adapted to measure the amount of luminous radiation to which the kit is exposed, and generates events that are stored into the memory of the device every time the light intensity exceeds a preset threshold for a given time interval, preferably every time the product between light intensity and exposition time exceeds a value which is considered to be unsafe for the kit's integrity.

In a non-limiting embodiment, the light sensor in use belongs to the family normally employed for detecting environmental light; it behaves like a human eye in a wide variety of illumination conditions, and is therefore sensitive to frequencies within the visible range. Said sensor is available in a basic version with analog output or in an enhanced version with lux output. In this case, the device contains a photodiode and an ADC converter, both integrated into a single CMOS. Moreover, in accordance with a low-consumption strategy, it provides two operating modes: low power mode and active mode.

Another very important parameter that must be taken into account when evaluating the stability of some reagents, i.e., their capability of maintaining their characteristics within a certain range of values defined by the manufacturer until their expiry date, is the electric conductivity of the solution. For many of these substances, it is essential that electric conductivity be checked. Since flow of electric current in a solution is possible because of the motion of the ions contained therein, the conductivity of a solution increases with the concentration of ionic species and depends on:
  type of ionic charge,
  velocity of migration of the ions in the solution or mobility,
  temperature,
  pressure,
  viscosity of the solvent,
  dielectric nature of the solvent.

Electric conductivity is a parameter that can provide much information about the state of alteration of the reagents' chemical-physical characteristics. In particular, it is a solution concentration index, which is fundamental in this specific field of application. In fact, equal volumes of a solution with different concentrations transport a different quantity of active principle, thus altering the measurement, which depends on specific quantities of components. Electric conductivity also allows to determine reagent oxidation, e.g., due to an imperfectly sealed cuvette.

In a non-limiting embodiment, the electric conductivity sensor consists of two gold-plated or platinum-plated electrodes placed directly in contact with the solution. The electrodes must have good chemical stability until the reagents' expiry date. The very low currents considerably reduce the degradation of the sensitive electrode, thus making it very suitable for long, low-power measurements. The electronic conditioning and measurement part operates on AC, typically at 10 kHz, with very low voltages, and measurements can be carried out daily or upon request.

The electric conductivity sensor is an integrated circuit that is placed in the reagent cuvette, and requires two small electrodes inserted into the container by using a low-cost deposition or "overmolding" technique. The particular structure of the sensor is due to the fact that the electrodes must be in direct contact with the solution in order to be able to measure the conductivity thereof.

The reagent kit is very sensitive to variations such as orientation changes and vibrations. Therefore, the MEMS accelerometer is adapted to carry out the function of detecting the conditions of:

Position/orientation, e.g., vertical storage, storing overturning events (vertical Z axis of the MEMS sensor);

Acceleration, due to fast movements, e.g., when using the kit in different analytical systems, storing accelerometric events exceeding a certain threshold;

Vibrations, e.g., when opening and closing the kit, with detection of the mixing state of the solid phase in the container 23, storing accelerometric events exceeding thresholds on multiple axes.

The microcontroller integrated into the ASIC is of the type characterized by minimal consumption, and is programmed for periodically executing acquisition and event wake-up operations. The device can operate in two modes, depending on the availability of a radio-frequency connection with the reader, ensuring transfer of logged information and programming of functions and intervention thresholds.

The system is designed for use of a flexible printed circuit board on which the chip and a few auxiliary components (capacitor, inductive antenna and some sensors) are arranged.

The battery is placed in a suitable seat formed in the plastic support, and is directly connected to the flexible circuit.

The conductivity sensor provides for sensitive elements inserted into the bottom of the containers, in contact with the fluid under examination and wired to the printed circuit board.

Figure 3:
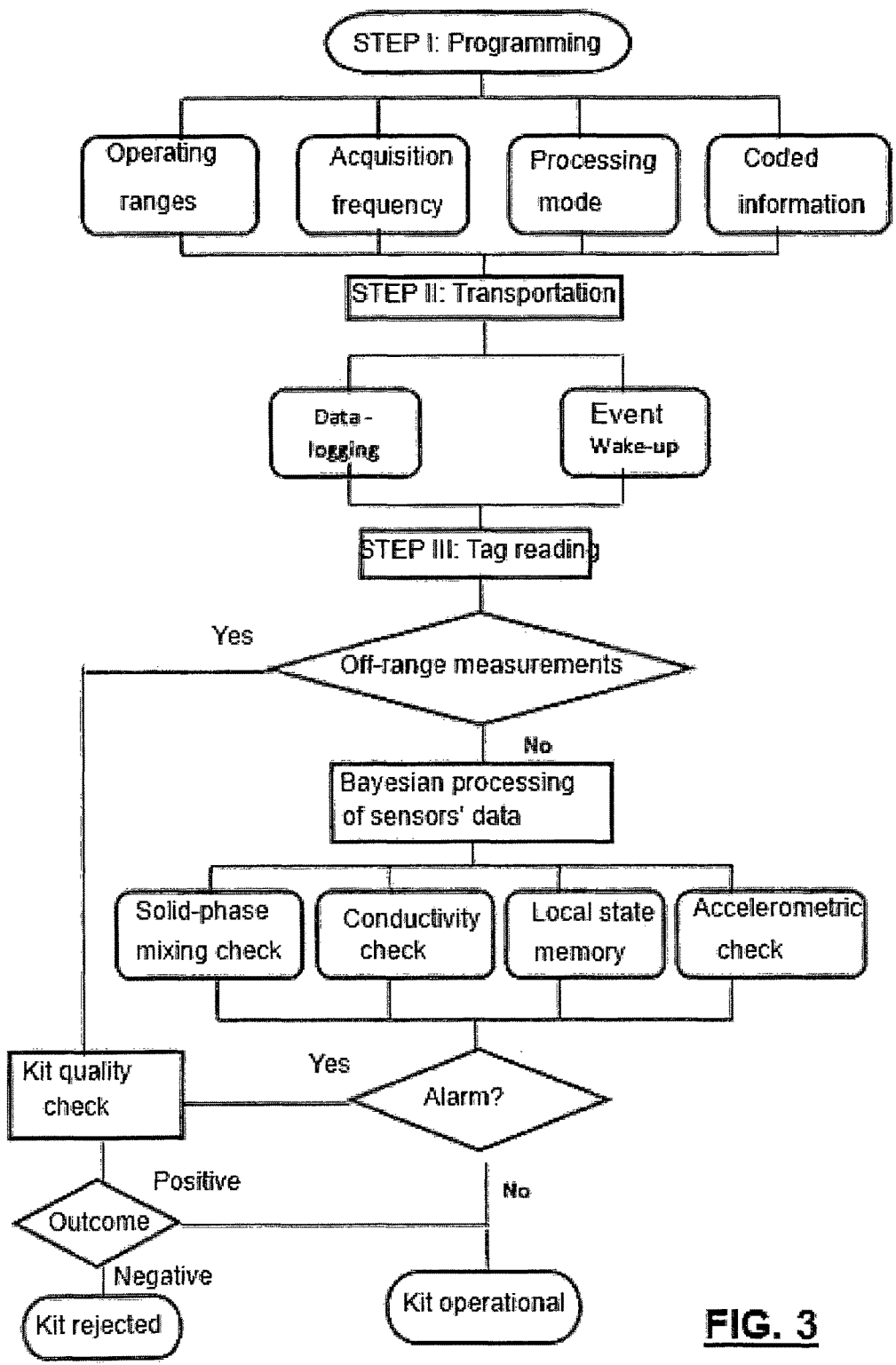
FIG. 3 shows a flow chart of the method for identifying and monitoring the reagent kit.

The following will describe the method for identifying and monitoring the reagent kit according to the invention, with reference to the operational flow chart of FIG. 3.

The method essentially comprises three steps: a first step of programming the identification and monitoring device; a second step of monitoring and logging data while transporting the device; a third step of verifying and processing the monitoring data.

In the first step, while programming the identification and monitoring device and installing it into the reagent kit, the system's adjustment and configuration parameters are defined and stored, such as:

Operating ranges
Parameter acquisition frequency
Processing modes
Coded information The second step of monitoring and logging data starts at the end of the step of composing the reagent kit, until the reagent kit is installed into the analytical system.

During this step, the physical quantities being monitored are stored into the device on the basis of two types of detections:

data logging: parameters such as temperature and conductivity are periodically detected, according to a period determined in the first step, and are then acquired and stored;

event wake-up: some parameters not requiring continuous detection, such as light or acceleration, are detected upon occurrence of anomalous or out-of-range events; acquisition and storage only occur at said instants, associated with the time of occurrence.

For example, at said instants the detection component (accelerometer or light sensor) can emit a "wake-up" or "interrupt" signal towards the microprocessor, which will then start acquisition and storage.

The third step of verifying and processing the monitoring data acquired during the second step starts after the reagent kit has been installed into the analytical system, and goes on while using the kit.

The verification and processing of the monitoring data are aimed at providing the following functionalities:

Identification of causes and solutions of problems related to the use of the kit The logged temperature, light and acceleration data can be further processed to detect any improper reagent transportation or handling conditions. For example, the light exposure data can be compared with the instant at which the kit was inserted into the analytical system in order to calculate the time interval that has elapsed from the instant when the package was opened to the moment of actual use thereof.

Continuous measurement of the number of uses (tests) available (number of opening/closing actions)

From the accelerometric data, or anyway from information directly coming from the analyzer, it is possible to calculate the number of opening and closing actions carried out, and hence the number of tests carried out; this datum can then be updated by writing it to the RFID tag of that particular kit. Thus, should the operator have to move a kit not yet exhausted from one machine to another, it will be possible to know the number of remaining tests still available for that kit by reading it from the RFID tag.

Management of risk indices related to the use of the current kit (pre-alarm and alarm condition)

If anomalous transportation/handling conditions are inferred from the analysis of the data, it is possible to activate warning or danger signals when inserting the kit into the machine and, based on the level of severity of such conditions, either a quality check prior to use or immediate replacement will be recommended.

Detection of defects in the stirring or mixing of the solid phase

Since in specific applications a part of the reagent kits must be continuously mixed during use, from the analysis of the accelerometric data it is possible to detect possible error situations and warn the operator, who will then be able to remedy.

The data may be processed, for example, by software installed in the computer controlling the analytical system or in a remote server, to which such data are sent as soon as the reagent kit has been transferred aboard the machine.

The processing is carried out according to the known Bayesian processing technique. This is a method of determining the probability of verisimilitude of given events: it is an approach to statistical inference wherein probability is not interpreted as frequency, proportion or similar concepts, but rather as degrees of belief (likelihood) in the occurrence of a given event.

Within this frame, wherein multiple sensors are present, the contributions of the various signals emitted by the sensors are weighted in order to obtain more sophisticated information. In fact, it is believed that each sensor, taken individually, would not be able to provide complete information, e.g., about the degree of reliability or preservation of the kit, whereas combined detections of multiple sensors can provide it, so that a decision about the kit's reliability can be made. For example, if a parameter is out of range, but the other parameters are aligned and within range, the decision may be that the kit must be considered as good.

More in particular, with reference to FIG. 3, the software part involved in the third step provides for making an iterative check, particularly a deterministic one, for off-range measurements, i.e., for verifying the monitoring data: if the measurements are not within acceptable values, the kit is subjected to a quality check, the outcome of which may be either positive, in which case the kit will be considered to be in a normal and acceptable operational condition, or negative, in which case the kit will be discarded and replaced.

If the outcome of the check for off-range measurements is positive, the above-defined Bayesian processing will be carried out. In particular, the parameters to be processed are: solid-phase stirring check, conductivity check, local state memory check, and accelerometer check.

The iterative outcome of the Bayesian processing may be either positive, in which case the kit will be considered to be operational, or negative, in which case an alarm signal will be issued, which will originate a kit quality check as described above.

The present invention can advantageously be implemented through firmware or by integrating the on-board software of the analytical machine for the execution of one or more steps of the methods described herein. It is therefore understood that the protection scope extends to said programs as well as to computer-readable means that comprise a recorded message, said computer-readable means comprising program coding means for implementing one or more steps of the method when said program is executed by a computer or by a microcontroller, microprocessor, ASIC or FPGA.

The above description of some embodiments of the invention has made more apparent the reasons why applications of various known types of sensors, or known passive or active RF-ID devices, in technical fields other than the specific field of designing an analytical system and a reagent kit cannot be obviously used in the latter, the main classes of reasons being the following three:
structural configuration;
typology of applied sensors;
processing algorithm.

As far as the first aspect is concerned, it is necessary to take into account the constraints imposed by the particular structure of the reagent kit and of that part of the analytical system which is to accommodate said kit. The small dimensions compel to integrate all the modules required for the operation of the device, i.e., the sensing, processing and power parts, into a single, small device that can be applied to the reagent kit. The point of application of the device according to the invention must be such as to not create any conflicts with adjacent reagent kits and to allow establishing a short-range wireless connection to an RFID reader suitably arranged inside the analytical system, in the immediate vicinity of the kit housing section.

Moreover, the applied sensors cannot be of the tape type as described in US2010/0180701-A1, because they cannot be integrated into an ASIC. Some of them may require a specific type of construction, as will be described below, allowing them to be in close contact with the liquid the parameters of which are to be measured.

As regards the processing algorithm, the specificity of the different components of the reagent kit requires the use of information from the sensors as a function of the chemical, thermal and kinematic characteristics associated with the compounds.

The above-described example of embodiment may be subject to variations without departing from the protection scope of the present invention, including all equivalent designs known to a man skilled in the art.

The elements and features shown in the various preferred embodiments may be combined together without however departing from the protection scope of the present invention.

The advantages deriving from the application of the present invention are apparent.

The main advantage that is derived from this invention is that it is possible to store into the memory of the device all the data recorded by the sensors during the whole period between kit production and kit exhaustion.

When the reagent kit is inserted into the analyzer, by simply reading the tag it is possible to trace a kit history through an analysis of the data, and then evaluate the state of preservation and manipulation of the kit to avoid any criticality during the next analytical stage.

By processing the data it is possible to detect possible error or risk situations, which can then be immediately remedied, thus saving time and resources.

Such a solution confers much added value on the product, because the operator can be certain that the analytical performance of the reagents have not undergone any significant alterations along the path from the manufacturer to the user, and that such performance is that guaranteed by the quality check.

The information acquired by the device is also useful for the manufacturer itself in view of handling possible customer's complaints, which can be replied to more quickly because it is possible to go back to the events that caused the performance degradation.

Furthermore, by suitably processing the data it is possible to establish correlations between the monitored parameters and the kit's performance, and thus comprehend mechanisms which are very important for constantly improving the stability and quality of the reagents. From the above description, those skilled in the art will be able to produce the object of the invention without introducing any further construction details.

The invention claimed is:

1. A device adapted to identify and monitor a reagent kit adapted for insertion into an analytical system, wherein the device is positioned in said reagent kit and comprises:
a first measurer configured to measure a temperature of the reagent kit;
a second measurer configured to measure a light level to which the reagent kit is subjected;
a third measurer configured to measure an electric conductivity level of one or more reagents of the reagent kit, said third measurer being in contact with said one or more reagents;
a fourth measurer configured to measure a triaxial acceleration to which the reagent kit is subjected;
a multiparameter data-logger configured to log data obtained from said temperature, light, conductivity and acceleration measurers both prior to and after insertion of the reagent kit into the analytical system;
a circuit for storing and transmitting data identifying the reagent kit and said data obtained from said temperature, light, conductivity and acceleration measurers to said analytical system, and for detecting wake-up or interrupt detection signals coming from said measurers, wherein the reagent kit is evaluated using the transmitted data at least one of prior to insertion of the reagent kit into the analytical system and after insertion of the reagent kit into the analytical system to detect operational or non-operational conditions.

2. The device according to claim 1, wherein said circuit for storing and transmitting data identifying the reagent kit comprises a TAG-RFID with a short-range transponder.

3. The device according to claim 1, wherein said first measurer is adapted to measure temperature values at regular time intervals starting from an activation instant, until the reagent kit is inserted into the analytical system.

4. The device according to claim 1, wherein said second measurer is adapted to measure a luminous radiation amount to which said reagent kit is subjected, and to generate events to be stored into said circuit for storing every time said light level exceeds a preset threshold for a given time interval.

5. The device according to claim 4, wherein the second measurer is generates events to be stored into the circuit for storing every time the product between light level and exposition time exceeds a threshold value.

6. The device according to claim 1, wherein said third measurer comprises one or more pair of electrodes in contact with respective reagents included in the kit, and are adapted to measure the electric conductivity of said reagents at regular time intervals.

7. The device according to claim 1, wherein said fourth measurer is adapted to detect the conditions of:
position/orientation of the kit, storing overturning events;
acceleration of the kit, storing accelerometric events exceeding a threshold;
vibration of the kit, storing accelerometric events exceeding thresholds on multiple axes.

8. A method for identifying and monitoring a reagent kit of an analytical system, which is adapted to use data received from a device adapted to identify and monitor the reagent kit as claimed in claim 1, for the purpose of detecting operational or non-operational conditions of said kit, the method comprising:

programming an identification and monitoring device, wherein adjustment and configuration parameters are stored into the identification and monitoring device, wherein the identification and monitoring device is associated with the reagent kit;

transporting the reagent kit, and monitoring and logging data with the device while transporting the reagent kit wherein data obtained from said temperature, light, conductivity and acceleration measuring means are monitored and logged on the basis of a periodic type of detection and a type of detection which is carried out when anomalous or out-of-range values of said data have been read;

inserting the reagent kit into the analytical system;

verifying and processing the monitoring data after having inserted the reagent kit into the analytical system, wherein operations are carried out for:

identifying the causes of and solving problems related to the use of the kit on the basis of data obtained by means of said periodic type of detection, said data being the light exposure data compared with the instant at which the kit was inserted into the analytical system, said identification being performed by calculating the time interval that has elapsed from the instant when the kit was opened to the moment of actual use thereof;

managing kit use risk indices, namely pre-alarm and alarm conditions, on the basis of data obtained by means of said type of detection which is carried out when anomalous or out-of-range values have been read, by activating warning or danger signals when inserting the kit into the machine;

detecting defects in the mixing of the solid phase, by using said acceleration measurements, and emit warning signals.

9. The method according to claim 8, wherein said operations comprised in the third step are carried out on the basis of a Bayesian processing of the data.

* * * * *